United States Patent
Roos

(10) Patent No.: US 7,288,219 B1
(45) Date of Patent: Oct. 30, 2007

(54) METHOD AND APPARATUS FOR SIZE MEASUREMENT OF PARTICLES OF CARBON BLACK

(76) Inventor: Ermi Roos, 7315 SW. 79th Ct., Miami, FL (US) 33143

( * ) Notice: Subject to any disclaimer, the term of this patent is extended or adjusted under 35 U.S.C. 154(b) by 0 days.

(21) Appl. No.: 11/512,843

(22) Filed: Aug. 30, 2006

(51) Int. Cl.
*H01B 1/00* (2006.01)

(52) U.S. Cl. .................. 252/500; 324/71.4; 324/92; 324/93; 324/94

(58) Field of Classification Search .......... 252/500; 205/790.5, 794.5; 324/71.4, 92–94
See application file for complete search history.

(56) References Cited

U.S. PATENT DOCUMENTS 2,656,508 A  10/1953  Coulter
3,815,024 A   6/1974  Bean
4,157,498 A * 6/1979  Johnson ............... 324/71.1

OTHER PUBLICATIONS

U.S. Appl. No. 11/329,829, Roos.
De Blois And Bean, Rev. Sci. Inst. Jul. 1970, vol. 41, No. 7. p. 909 American Institute of Physics, College Park, MD.

* cited by examiner

*Primary Examiner*—Douglas McGinty
*Assistant Examiner*—Jaison Thomas

(57) ABSTRACT

Improvements to the electrical sensing zone instrument are described that allow the good accuracy of this type of instrument to be applied to the measurement of the size of particles of carbon black. The improvements include a concentrated aqueous electrolyte containing KI or NaI, a surfactant soluble in the electrolyte capable of dispersing particles of carbon black, and an anode electrode that is made of silver at the surface touching the electrolyte. The silver anode electrode prevents the degradation of the electrolyte by light and electrolysis.

1 Claim, 1 Drawing Sheet

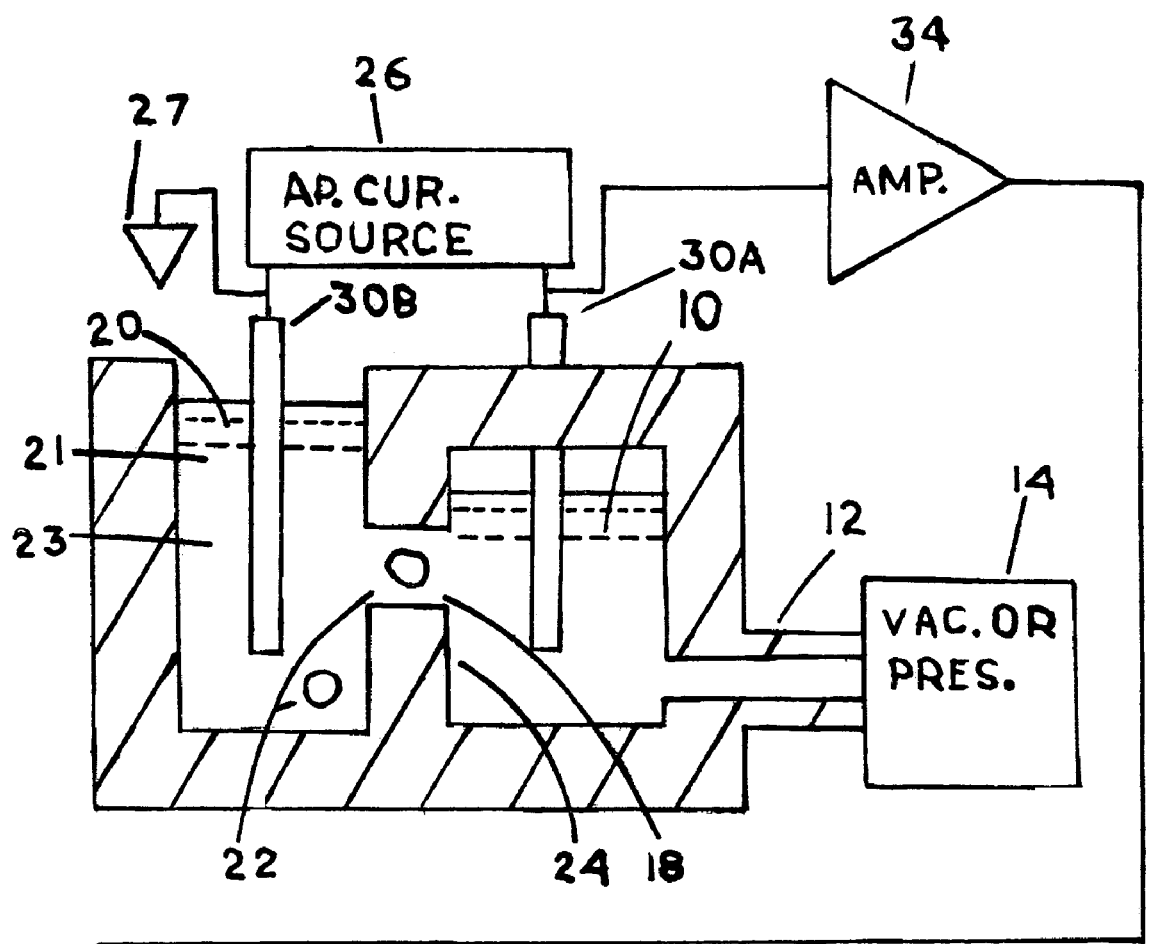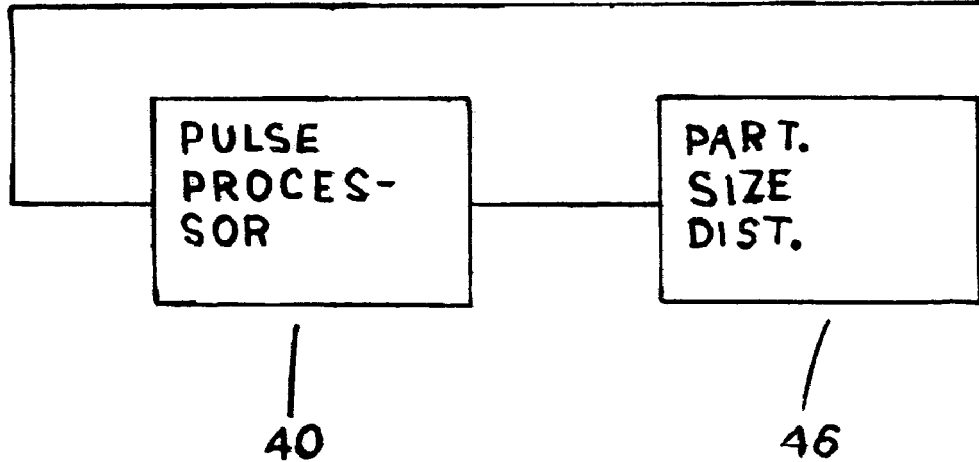

METHOD AND APPARATUS FOR SIZE MEASUREMENT OF PARTICLES OF CARBON BLACK

BACKGROUND

1. Field of the Invention

The present invention relates to a method and apparatus for size measurements of particles of carbon black.

2. Description of the Related Art

Carbon black is a material of great industrial importance. It is formed by the incomplete combustion of certain fuels containing carbon. One of its major uses is to strengthen rubber tires. It is carbon black that gives tires their black color. It is also used to make black ink and black pigments, and toners for copy machines and printers. Every application of carbon black requires control of its particle size distribution. For example, tires require larger particle sizes than pigments and inks. To control the particle size distribution requires first being able to measure it. Carbon black particles are particularly difficult to measure because they are very small. A typical carbon black sample contains particles in the range of 40 manometers (nm) to one micrometer (μm) in diameter.

The standard method of measuring the particle size distribution of carbon black is using a transmission electron microscope (TEM) with an automated image analyzer. The particles are too small to be measured using an optical microscope. The procedure for using the TEM is very difficult and time-consuming to perform, and easier and faster methods have been tried. Centrifugal sedimentation has been used, but the parameter that is measured, Stokes diameter, is not a good representation of particle size. A non-spherical particle can be measured to have a wide range of Stokes diameters. The orientation of the particle with respect to its direction of travel affects the measured Stokes diameter. Laser diffraction analyzers have also been used, but they lack both the sensitivity and accuracy needed for measuring carbon black particles. In fact, laser diffraction analyzers are very inaccurate when measuring any particles that are not spherical in shape. The inherent inaccuracy is so great that it is incorrect to call laser diffraction analyzers particle size measurement instruments. Their reproducibility is very good, however, and the same sample is likely to be measured with nearly the same incorrect results every time. Electrical sensing zone (ESZ) instruments have also been used, but, while they have very good accuracy, they usually do not have enough sensitivity for measuring carbon black particles.

The ESZ instrument was first described in U.S. Pat. No. 2,656,508, issued to Coulter on Oct. 20, 1953. Some features thereof are shown in the Drawing. A particle 22 is measured by passing it through an electrical current-carrying aperture 18 between insulating containers 10, 20 holding a conductive liquid 21. The motion of particles through the aperture 18 is caused by a pressure difference across a partition 24 between the insulating containers 10, 20 produced by a vacuum or pressure source 14. The presence of a particle 22 in the aperture 18 increases the electrical resistance of the aperture 18 by displacing liquid 21 of equal volume to the particle 22 volume. The change in resistance may be detected as an increase in voltage across the aperture 18, or a decrease in current through the aperture 18. The change in resistance is approximately proportional to the volume of the particle 22. It is this approximate proportionality between aperture 18 resistance and particle 22 volume that gives the ESZ method high accuracy compared to several other methods of particle 22 size measurement. It does not matter if the particles 22 are electrically conducting or not, because all particles 22 in an ESZ instrument behave as if they are electrical insulators.

The sensitivity of the ESZ instrument can be increased by making the effective volume of the aperture 18 smaller. The smallest apertures 18 available commercially for ESZ instruments are not small enough for measuring the finer grades of carbon black particles 22. Usually, an aperture is made by boring a small hole through a thin sapphire wafer. The effective volume of the aperture can be made smaller by reducing the diameter of the hole, and making the sapphire wafer thinner. Unfortunately, a wafer thinner than about 30 μm is easily broken during normal operation of the ESZ instrument, and great care must be used to avoid breakage. U.S. Pat. No. 3,815,024, issued Jun. 4, 1974 to Bean and De Blois, describes a method of making very small apertures that can measure very small particles, but these are even more delicate than the small sapphire aperture mentioned above. The material used is polycarbonate, which has much less flexure strength and resistance to breakage than sapphire. My co-pending application Ser. No. 11/329,829, filed Jan. 12, 2006, describes a way to make an aperture of low effective volume that is resistant to breakage.

The medium carrying particles 22 through the aperture 18 is an aqueous electrolyte 21. Any given volume of electrolyte has a finite number of ions. This finite number produces a shot noise phenomenon that causes the noise to increase as the electrical current through the aperture 18 increases. An article by De Blois and Bean that describes their invention in greater detail than their aforementioned patent, in Rev. Sci. Inst. Vol. 41 No. 7, p. 909, 1970, mentions the shot noise, but does not identify the cause as the finite number of ions. The shot noise, which is lowest for uni-univalent electrolytes 21, decreases as the ion concentration increases. It is therefore desirable to use as high an electrolyte 21 concentration as possible. Unfortunately, it is difficult to disperse very small particles in highly concentrated electrolytes. The concentration that is typically used in an ESZ instrument is in the vicinity of 1% by weight of sodium chloride (NaCl). This concentration is high enough to screen electrostatic forces at the surfaces of the particles 22, and electrostatic repulsion cannot be used to keep the particles 22 separated from each other. Thus, to keep the particles 22 dispersed, a surface-active agent (surfactant) 23 must be added to the electrolyte 21. A surface-active agent 23 will usually not work if the equivalent concentration is more than about 4% by weight of NaCl. This is because high concentration can cause some of the surface-active agent 23 to flocculate and precipitate. The portion of the surface-active agent 23 still in suspension forms large micelles, which are detectable as noise by the ESZ instrument. If it were possible to increase the concentration further, and still keep particles 22 dispersed, noise could be reduced further. The prior art methods do not permit higher ionic concentrations in the ESZ instrument if very small particles 22 are used.

SUMMARY OF THE INVENTION

The instant invention describes an apparatus and method for using the highly accurate ESZ instrument for measuring carbon black particles.

OBJECTS AND ADVANTAGES

It is one of the main objects of the present invention to increase the signal-to-noise ratio of the ESZ instrument while measuring carbon black particles by using an electrolyte, surfactant, and electrode combination that allows the very small (less than a particle diameter of about 0.5 μm) carbon black particles to be suspended in more concentrated electrolyte than was previously possible. This is the equivalent of greater than 10% by weight (about 2 gram-moles per liter) concentration of NaCl. The use of very concentrated electrolyte reduces the noise in the aperture and allows smaller particles to be measured.

It is another object of this invention to provide an alternative method to electron microscopy for accurately measuring the size of carbon black particles. The alternative method should be easier and faster to use than electron microscopy.

It is still another object of the present invention to measure a larger number of particles of carbon black in a sample than is possible using a TEM and an image analyzer, thus increasing the statistical accuracy of the particle size distribution measurement.

Yet another object of the invention is to provide a more accurate alternative to measuring the size of carbon black particles than centrifugal sedimentation and laser diffraction analysis, as well as several other particle size measurement methods.

It is also another object of this invention to provide such a device that is inexpensive to manufacture and maintain while retaining its effectiveness.

Further object of the invention will be brought out in the following part of the specification, wherein detailed description is for the purpose of fully disclosing the invention without placing limitations thereon.

BRIEF DESCRIPTION OF THE DRAWING

With the above and other related objects in view, the invention mostly consists in the details of compositions of homogeneous materials of certain components of a prior art electrical sensing zone (ESZ) apparatus. The invention will be more fully understood from the following description, when read in conjunction with the accompanying drawing, which is a schematic diagram applicable to both the instant invention and the prior art ESZ apparatus. Drawings of the compositions of the homogeneous materials that distinguish the instant invention from the prior art are not required for an understanding thereof.

REFERENCE NUMERALS IN DRAWING 10 nearly closed container
12 tube to vacuum or pressure source
14 vacuum or pressure source
18 aperture
20 open container
21 aqueous electrolytic solution
22 particle of the sample to be measured by the instrument
23 surface-active agent (surfactant)
24 partition containing the aperture
26 aperture current source
27 ground connection
30A electrode in nearly closed container
30B electrode in open container
34 amplifier
40 pulse processor
46 particle size distribution recorder

DETAILED DESCRIPTION OF THE PREFERRED EMBODIMENT

Referring now to the drawing, where both the present invention and a prior art ESZ instrument are shown in general terms, the particles 22 being measured are presumed to be composed of carbon black, and the homogeneous material that distinguishes the present invention from the prior art comprises the chemical composition of aqueous electrolytic solution 21, the chemical composition of surfactant 23, and the chemical composition of the anode electrode, which can be either 30A or 30B, depending on which electrode has a positive polarity. The apparatus will function equally well if either electrode is selected to be the anode.

The present invention is based upon my conjecture that the reason surfactant 23 does not usually disperse very small particles 22 in a very concentrated electrolytic solution 21 is because of what is commonly known as the "salting out" effect. Salting out is the reduction of the solubility of a substance in solution due to the addition of an electrolytic solute to the solution. While I believe that my conjecture is correct, I don't wish to be bound by it. I have observed that high concentrations of NaCl and potassium chloride (KCl), the most common electrolytes 21 used in ESZ instruments, cause several kinds of surfactants 23 to flocculate, while potassium iodide (KI) and sodium iodide (NaI) often do not. I have also observed that if the surfactant 23 used with concentrated KI or NaI is octylphenol-ethylene oxide, commonly known in the scientific community by the trademarks Nonidet P-40 and Polydet P-40, carbon black particles can be dispersed using an ultrasonic probe to agitate the particles sufficiently vigorously so that they form a colloidal suspension. Several of the surfactants 23 I tested did not flocculate in concentrated KI or NaI, but they were still not capable of dispersing carbon black. Thus, although it is necessary for a surfactant 23 to dissolve in an electrolyte 21 to disperse particles 22 in the electrolyte 21, not all particles 22 can be dispersed in a particular surfactant 23 and electrolyte 21 combination.

The ability of NaI and KI to dissolve surface-active agents 23 decreases with exposure to light because light causes iodine ($I_2$) to be released into solution. Placing a piece of silver (Ag) in the KI or NaI solution reverses the production of $I_2$ by forming silver iodide (AgI). AgI is soluble in concentrated KI and NaI solution. Electrolysis produced at the anode electrode, 30A or 30B, during the normal operation of the ESZ instrument also causes 12 to be released into solution. This does not happen if the anode electrode is made of Ag, or is coated with Ag where the anode electrode touches the electrolyte.

The foregoing description conveys the best understanding of the objectives and advantages of the present invention. Different embodiments may be made of the inventive concept of this invention. It is to be understood that all matter disclosed herein is to be interpreted merely to be illustrative, and not in a limiting sense.

What is claimed is:

1. An electrical sensing zone apparatus for measuring carbon black particle size, comprising:
   A) a uni-univalent aqueous electrolyte of at least 2 gram moles per liter concentration, said electrolyte selected from a group consisting of potassium iodide and sodium iodide;
   B) a surfactant wherein said surfactant comprises octylphenol-ethylene oxide and
   C) an anode electrode in said electrical sensing zone apparatus made of silver where said electrode touches said electrolyte.

* * * * *

UNITED STATES PATENT AND TRADEMARK OFFICE
CERTIFICATE OF CORRECTION

| | |
|---|---|
| PATENT NO. | : 7,288,219 B1 |
| APPLICATION NO. | : 11/512843 |
| DATED | : October 30, 2007 |
| INVENTOR(S) | : Ermi Roos |

Page 1 of 1

It is certified that error appears in the above-identified patent and that said Letters Patent is hereby corrected as shown below:

Col. 4, line 41, change "causes 12 to be released" to --causes $I_2$ to be released--.

Signed and Sealed this

Fourth Day of March, 2008

JON W. DUDAS
*Director of the United States Patent and Trademark Office*